United States Patent
Han et al.

(10) Patent No.: US 10,874,636 B2
(45) Date of Patent: Dec. 29, 2020

(54) APPLICATION OF SUBSTITUTED CINNAMAMIDE DERIVATIVES IN PREPARATION OF ANTI-ANXIETY MEDICATION

(71) Applicant: TASLY PHARMACEUTICAL GROUP CO., LTD., Tianjin (CN)

(72) Inventors: Min Han, Tianjin (CN); Xiaohui Ma, Tianjin (CN); Wangyi Zhou, Tianjin (CN); Yanyong Liu, Tianjin (CN); Yanchuan Li, Tianjin (CN); Jing Wang, Tianjin (CN); Shuiping Zhou, Tianjin (CN); He Sun, Tianjin (CN); Yonghong Zhu, Tianjin (CN)

(73) Assignee: Tasly Pharmaceutical Group Co., Ltd., Tianjin (CN)

( * ) Notice: Subject to any disclaimer, the term of this patent is extended or adjusted under 35 U.S.C. 154(b) by 0 days.

(21) Appl. No.: 16/073,507

(22) PCT Filed: Jan. 20, 2017

(86) PCT No.: PCT/CN2017/071898
§ 371 (c)(1),
(2) Date: Jul. 27, 2018

(87) PCT Pub. No.: WO2017/129061
PCT Pub. Date: Aug. 3, 2017

(65) Prior Publication Data
US 2019/0046500 A1 Feb. 14, 2019

(30) Foreign Application Priority Data
Jan. 27, 2016 (CN) .......................... 2016 1 0053180

(51) Int. Cl.
*A61K 31/36* (2006.01)
*A61K 31/357* (2006.01)
(Continued)

(52) U.S. Cl.
CPC .......... *A61K 31/357* (2013.01); *A61K 31/166* (2013.01); *A61K 31/4525* (2013.01);
(Continued)

(58) Field of Classification Search
CPC ................ A61K 31/357; A61K 31/166; A61K 31/4525; A61K 31/496; A61K 31/165;
(Continued)

(56) References Cited

U.S. PATENT DOCUMENTS

| 3,431,302 A | 3/1969 | Brown |
| 6,900,354 B2 | 5/2005 | Jolidon et al. |

(Continued)

FOREIGN PATENT DOCUMENTS

| CN | 1665774 A | 9/2005 |
| CN | 102775394 A | 11/2012 |

(Continued)

OTHER PUBLICATIONS

David Baldwin, Robert Woods, Richard Lawson, David Taylor, Efficacy of drug treatments for generalised anxiety disorder: systematic review and meta-analysis, BMJ 2011;342:d1199 doi:10.1136/bmj.d1199 (Year: 2011).*
NIMH—Generalized Anxiety Disorder (Year: 2020).*
Gunia-Krzyzak et al.; "Cinnamamide Derivatives for Central and Peripheral Nervous System Disorders—A Review of Structure-Activity Relationships"; ChemMedChem; vol. 10 Issue 8; Aug. 2015; p. 1302-1325.
International Patent Application No. PCT/CN2017/071898; Int'l Written Opinion and the Search Report; dated Apr. 12, 2017; 11 pages.
Han et al.; "Synthesis and structure-activity relationship of novel cinnamamide derivatives as antidepressant agents"; Bioorganic & Medicinal Chemistry Letters; vol. 24; 2014; p. 5284-5287.
Jacobson et al.; "Avoidance mediates the relationship between anxiety and depression over a decade later"; Journal of Anxiety Disorders; vol. 28; 2014; p. 437-445.

(Continued)

*Primary Examiner* — Sarah Pihonak
*Assistant Examiner* — Jason Deck
(74) *Attorney, Agent, or Firm* — BakerHostetler

(57) ABSTRACT

Disclosed is an application of substituted cinnamamide derivatives in the preparation of anti-anxiety medications, the substituted cinnammide derivatives are compounds having the structure of formula (I) or pharmaceutically acceptable salts thereof, wherein, $R_1$ is —H, —OH, —F, —Cl, —Br, —I, —OCH$_3$, —OCF$_3$, —OCHF$_2$, —OCH$_2$F, —CF$_3$, —CHF$_2$, —CH$_2$F, —CH$_3$, —CH$_3$CH$_2$, —CF$_3$CH$_2$, —CN, —NO$_2$, —NH$_2$ or —COOR$_5$; $R_2$ is H, $C_1$-$C_{10}$ linear alkyl, $C_3$-$C_{10}$ branched alkyl, $C_3$-$C_{10}$ cyclic alkyl, $C_1$-$C_{10}$ hydroxyalkyl or a N-substituted piperazine-derived group; or $R_2$ is a group forming with adjacent Y a tetrahydropyrrolyl group, a piperidyl group or a cyclohexanimido group.

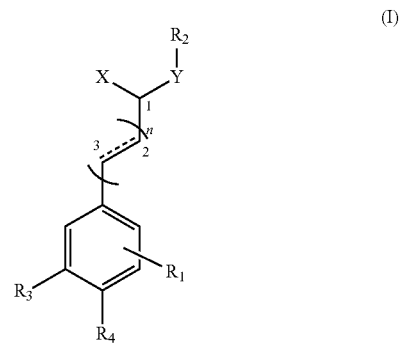

9 Claims, No Drawings

(51) Int. Cl.
*A61K 31/4525* (2006.01)
*A61K 31/166* (2006.01)
*A61P 25/22* (2006.01)
*A61K 31/496* (2006.01)
*C07D 317/60* (2006.01)
*C07C 235/34* (2006.01)
*C07D 295/192* (2006.01)

(52) U.S. Cl.
CPC ............ *A61K 31/496* (2013.01); *A61P 25/22* (2018.01); *C07C 235/34* (2013.01); *C07D 295/192* (2013.01); *C07D 317/60* (2013.01)

(58) Field of Classification Search
CPC .. A61K 31/36; A61K 31/4453; C07D 317/60; C07D 295/192; C07D 295/185; C07D 317/58; C07D 317/68; C07C 235/34; C07C 235/46; A61P 25/22
See application file for complete search history.

(56) References Cited

U.S. PATENT DOCUMENTS

| | | |
|---|---|---|
| 10,071,989 B2 | 9/2018 | Ma et al. |
| 2003/0166650 A1 | 9/2003 | Wu et al. |
| 2007/0049578 A1 | 3/2007 | Edwards et al. |
| 2007/0208083 A1 | 9/2007 | Kuehnert et al. |
| 2014/0121242 A1* | 5/2014 | Ma ........................ C07D 317/60 514/321 |

FOREIGN PATENT DOCUMENTS

| | | |
|---|---|---|
| CN | 102850317 A | 1/2013 |
| CN | 103826622 A | 5/2014 |
| CN | 104513172 A | 4/2015 |
| CN | 105085308 A | 11/2015 |
| EP | 2725018 A1 | 4/2014 |
| JP | 2004-535413 A | 11/2004 |
| JP | 2008-509199 A | 3/2008 |
| JP | 2014-523886 A | 9/2014 |
| RU | 2318802 C2 | 3/2008 |
| WO | WO-9723202 A1 * 7/1997 ........... C07D 209/16 |
| WO | WO 2004/007429 A1 | 1/2004 |
| WO | WO 2007/144169 A2 | 12/2007 |
| WO | WO 2011/080313 A1 | 7/2011 |
| WO | WO 2015/043522 A1 | 4/2015 |

OTHER PUBLICATIONS

European Patent Application No. 17743676.3; Extended Search Report; dated Jul. 31, 2019; 8 pages.

Schoffmann et al.; "Efficient Modulation of γ-Aminobutyric Acid Type A Receptors by Piperine Derivatives"; Journal of Medicinal Chemistry; vol. 57; 2014; p. 5602-5619.

* cited by examiner

APPLICATION OF SUBSTITUTED CINNAMAMIDE DERIVATIVES IN PREPARATION OF ANTI-ANXIETY MEDICATION

CROSS-REFERENCE TO RELATED APPLICATIONS

This application is the National Stage of International Patent Application No. PCT/CN2017/071898, filed Jan. 20, 2017, which claims the benefit of Chinese application number 201610053180.9, filed Jan. 27, 2016, the disclosures of which are incorporated herein by reference in their entireties.

TECHNICAL FIELD

The present invention relates to a new use of drugs, and more particularly, to an application of substituted cinnamamide derivatives in the preparation of anti-anxiety medications.

BACKGROUND ART

Anxiety disorder (also referred to as anxiety neurosis) is the most common among neuroses, which is mainly characterized by the experience of anxiety emotion. It can be divided into two forms: chronic anxiety (generalized anxiety) and acute anxiety attack (panic disorder). It mainly displays as nervousness and worry, restlessness attributable to undefined objective entities, and vegetative nervous symptoms (palpitation, hand trembling, sweating, frequent urination, etc.).

Specifically, in the case of chronic anxiety (also named as generalized anxiety), a patient would often present undue worry, nervousness and fear without obvious inducements, but there are generally no defined objects or contents leading to these manifestations. Its main manifestations are as follows: (1) emotional symptoms: jitters, scariness, terror, fear and apprehensiveness; (2) vegetative nervous symptoms: dizziness, chest distress, palpitation, tachypnea, dry mouth, frequent urination, urgent urination, sweating, tremor and other body-related symptoms; (3) psychomotor anxiety: restlessness, uneasiness, irritability, difficulties in staying calm.

In the case of acute anxiety attack (also named as panic attack or panic disorder), a patient would be suddenly caught in mental tension of supreme terror in a normal daily living environment without the presence of terrified situations, accompanied with the feeling of impending death or loss of control, and obvious symptoms of vegetative nervous system at the same time. Its main manifestations are as follows: (1) the feeling of impending death or loss of control: a patient would be suddenly caught in the state of mind of supreme terror, and thus experiences the feeling of impending death or loss of control; (2) symptoms of vegetative nervous system, such as chest distress, palpitation, dyspnea, sweating, systemic trembling, etc appear at the same time; (3) the time of duration is generally from several minutes to several hours: attacks begin suddenly, and a patient is conscious in the meantime.

In today's society, as people's life tempo speeds up, pressure at work increases, and social competition is becoming increasingly intense, the morbidity of anxiety disorders goes up year by year.

Anxiety disorder is generally treated with psychotherapy and drug therapy, wherein:

in the case of psychotherapy, a patient should find out the source of stress in life and avoid it, and learn relaxation techniques to relieve stress;

in the case of drug therapy, anti-anxiety medications are used to tranquilize hyperactive portions of the brain, and typical drugs are benzodiazepines (BDZ) drugs. These drugs have strong anti-anxiety effects and take effect rapidly, but their long-term administration has side effects, such as addiction, drug resistance and abstinence reactions etc; tricyclic antidepressants (TCAs) have good therapeutic effects on generalized anxiety, but their applications are limited by their strong anticholinergic side effects and cardiotoxic effects; other drugs for anxiety resistance are somehow faced with problems, such as slow onset of action, drug-drug interaction and adverse effects etc. The above side effects often make a patient full of concerns, which, in turn, exacerbates the patient's anxiety conditions or even compels the patient to abandon treatment. Furthermore, withdrawal reactions are the key challenge posed to doctors.

Therefore, there is an urgent need for a drug having effective therapeutic effects on anxiety and exhibiting few side effects. The cinnamamide derivatives of the present invention can pass rapidly across the blood-brain barrier after single oral administration, thereby playing their role in resisting against anxiety.

Cinnamamide is also called as benzyl acrylamide, cinnamic amide and 3-phenylacrylamide. Its substituted cinnamamide derivatives have once been disclosed in CN102850317A (application No.: CN201210123842.7) and CN104513172A (application No.: CN201410504555.X), which disclose a series of substituted cinnamamide derivatives and preparation methods thereof. It has been found through experimental researches on animals that substituted cinnamamide derivatives have obvious anti-depression activities.

There is no report about the effects of substituted cinnamamide derivatives on anxiety resistance.

The present invention relates to an application of substituted cinnamamide derivatives in the preparation of anti-anxiety medications. In the present invention, by investigating the effects of substituted cinnamamide derivatives on times of open-arm entries and residence time in the open-arms of mice during the elevated plus-maze test, as well as their effects on drinking times of rats during the punished session of the drinking conflict experiment, their effects on anxiety resistance are verified. These experiments showed that among the substituted cinnamamide derivatives, there are 17 compounds capable of increasing, in varying degrees, open-arm entries of mice seven days after administration, prolonging their open-arms time, and obviously increasing the drinking times of rats during the punished session of the drinking conflict experiment, thereby proving that substituted cinnamamide derivatives can be developed as anti-anxiety medications.

SUMMARY OF THE INVENTION

The present invention relates to a novel application of substituted cinnamamide derivatives.

Specifically, the present invention provides an application of substituted cinnamamide derivatives in the preparation of anti-anxiety medications.

wherein, the said anxiety refers to chronic anxiety (generalized anxiety) or acute anxiety (panic attack or panic disorder).

the said substituted cinnamamide derivatives are compounds having a structure of formula (I) or pharmaceutically acceptable salts thereof which serve as pharmaceutically active ingredients, as follows:

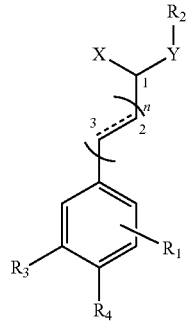

In the formula:

$R_1$ is —H, —OH, —F, —Cl, —Br, —I, —OCH$_3$, —OCF$_3$, —OCHF$_2$, —OCH$_2$F, —CF$_3$, —CHF$_2$, —CH$_2$F, —CH$_3$, —CH$_3$CH$_2$—, —CF$_3$CH$_2$—, —CN, —NO$_2$, —NH$_2$ or —COOR$_5$;

$R_2$ is H, $C_1$-$C_{10}$ straight chain alkyl, $C_3$-$C_{10}$ branched alkyl, $C_3$-$C_{10}$ cyclic alkyl, $C_1$-$C_{10}$ hydroxyalkyl or an N-substituted piperazine-derived group; or $R_2$ is a group formed as a tetrahydropyrrolyl group, a piperidyl group or a cyclohexanimido group with adjacent X;

each of $R_3$ or $R_4$ is independently H, OH, OR$_5$, F, Cl, Br, I, $C_1$-$C_{10}$ straight chain alkyl, $C_3$-$C_{10}$ branched alkyl, CF$_3$, CHF$_2$, CH$_2$F, NO$_2$, NH$_2$, OCF$_3$, OCHF$_2$, OCH$_2$F, OOCR$_5$ or COOR$_5$;

or $R_3$ and $R_4$ are linked to form —OCH$_2$O— or —OCH$_2$CH$_2$O—;

wherein $R_5$ is $C_1$-$C_{10}$ straight chain alkyl, $C_3$-$C_{10}$ branched alkyl, $C_3$-$C_{10}$ cyclic alkyl or $C_1$-$C_{10}$ hydroxyalkyl;

n is 1, 2 or 3, and —(C$_2$-C$_3$)$_n$— unit contains at least one carbon-carbon single bond or one carbon-carbon double bond;

X is =O, =S, H, SH or SR$_6$;

Y is N or NR$_6$, O or S;

$R_6$ is H, $C_1$-$C_{10}$ straight chain hydrocarbon, $C_3$-$C_{10}$ branched hydrocarbon, $C_3$-$C_{10}$ cyclic hydrocarbon or $C_6$-$C_{10}$ aromatic hydrocarbon;

preferably, the said substituted cinnamamide derivatives are as shown in formula (II):

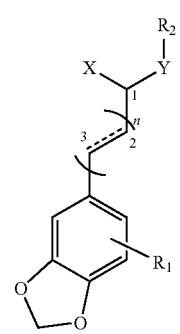

wherein, $R_1$ is —H, —OH, —F, —Cl, —Br, —I, —OCH$_3$, —OCF$_3$, —OCHF$_2$, —OCH$_2$F, —CF$_3$, —CHF$_2$, —CH$_2$F, —CH$_3$, —CH$_3$CH$_2$—, —CF$_3$CH$_2$—, —CN, —NO$_2$, —NH$_2$ or —COOR$_5$;

$R_2$ is H, $C_1$-$C_{10}$ straight chain hydrocarbon, $C_3$-$C_{10}$ branched hydrocarbon, $C_3$-$C_{10}$ cyclic hydrocarbon, $C_6$-$C_{10}$ aromatic hydrocarbon or $C_1$-$C_{10}$ alkyl alcohol or an N-substituted piperazine derivative; or $R_2$ is a group formed as a tetrahydropyrrolyl group, a piperidyl group or a cyclohexanimido group with adjacent X;

$R_5$ is $C_1$-$C_{10}$ straight chain alkyl, $C_3$-$C_{10}$ branched alkyl, $C_3$-$C_{10}$ cyclic alkyl or $C_1$-$C_{10}$ hydroxyalkyl;

n is 1, 2 or 3, and —(C$_2$-C$_3$)$_n$— unit contains at least one carbon-carbon single bond or one carbon-carbon double bond;

X is =O, =S, H, SH or SR$_6$;

Y is N or NR$_6$, O or S; wherein $R_6$ is H, $C_1$-$C_{10}$ straight chain hydrocarbon, $C_3$-$C_{10}$ branched hydrocarbon, $C_3$-$C_{10}$ cyclic hydrocarbon or $C_6$-$C_{10}$ aromatic hydrocarbon;

or preferably, the substituted cinnamamide derivatives are as shown in formula (III):

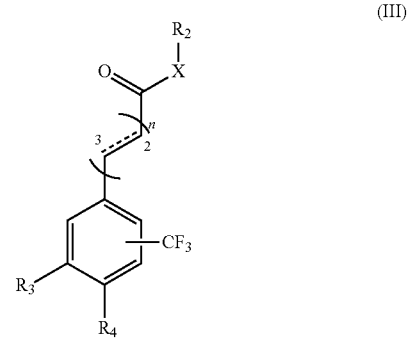

wherein, $R_3$ is H, OH, OR$_5$, F, Cl, Br, I, $C_1$-$C_{10}$ straight chain alkyl, $C_3$-$C_{10}$ branched alkyl, CF$_3$, CHF$_2$, CH$_2$F, NO$_2$, NH$_2$, OCF$_3$, OCHF$_2$, OCH$_2$F, OOCR$_5$ or COOR$_5$;

$R_4$ is H, OH, OR$_5$, F, Cl, Br, I, $C_1$-$C_{10}$ straight chain alkyl, $C_3$-$C_{10}$ branched alkyl, CF$_3$, CHF$_2$, CH$_2$F, NO$_2$, NH$_2$, OCF$_3$, OCHF$_2$, OCH$_2$F, OOCR$_5$ or COOR$_5$;

$R_5$ is $C_1$-$C_{10}$ straight chain alkyl, $C_3$-$C_{10}$ branched alkyl, $C_3$-$C_{10}$ cyclic alkyl or $C_1$-$C_{10}$ hydroxyalkyl;

n is 1, 2 or 3, and —(C$_2$-C$_3$)$_n$— unit contains at least one carbon-carbon single bond or one carbon-carbon double bond;

X is N or NH;

$R_2$ is H, $C_1$-$C_{10}$ straight chain hydrocarbon, $C_3$-$C_{10}$ branched hydrocarbon, $C_3$-$C_{10}$ cyclic hydrocarbon, $C_6$-$C_{10}$ aromatic hydrocarbon or $C_1$-$C_{10}$ alkyl alcohol or an N-substituted piperazine derivative; or $R_2$ is a group formed as a tetrahydropyrrolyl group, a piperidyl group or a cyclohexanimido group with adjacent X.

The compounds of the present invention or pharmaceutically acceptable acid addition salts thereof are particularly preferred as the following compounds:

5'-iodine-3',4'-methylenedioxy cinnamic acid isobutylamide (II-4)

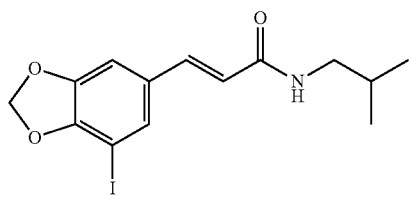 [SMILES: CC(C)CNC(=O)/C=C/c1cc(I)c2c(c1)OCO2]

5'-chlorine-3',4'-methylenedioxy cinnamic acid isobutylamide (II-4)

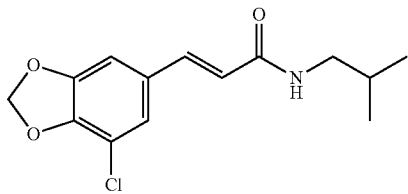 [SMILES: CC(C)CNC(=O)/C=C/c1cc(Cl)c2c(c1)OCO2]

5'-trifluoromethyl-3',4'-methylenedioxy cinnamic acid isobutylamide (II-5)

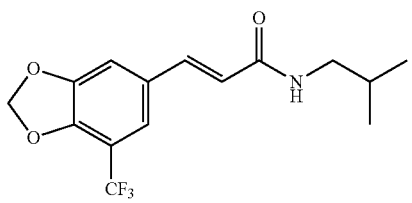

5'-trifluoromethyl-3',4'-methylenedioxy cinnamic acid piperidinylamide (II-10)

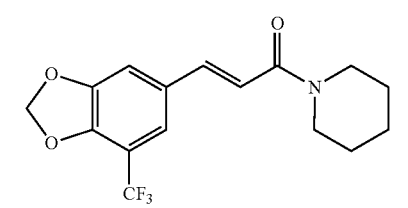 [SMILES: O=C(/C=C/c1cc2c(c(C(F)(F)F)c1)OCO2)N1CCCCC1]

3-(5'-trifluoromethyl-3',4'-methylenedioxy phenyl)-propionic acid isobutylamide (II-11)

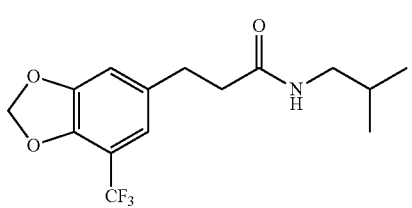 [SMILES: CC(C)CNC(=O)CCc1cc2c(c(C(F)(F)F)c1)OCO2]

5-trifluoromethyl-3',4'-methylenedioxy benzoic acid isobutylamide (II-12)

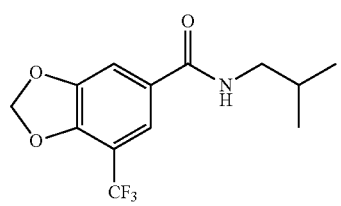 [SMILES: CC(C)CNC(=O)c1cc2c(c(C(F)(F)F)c1)OCO2]

(E)-N-(4-methylpiperazinyl)-5-(5'-trifluoromethyl-3',4'-methylenedioxy phenyl)-1-pentene amide hydrochloride (II-13)

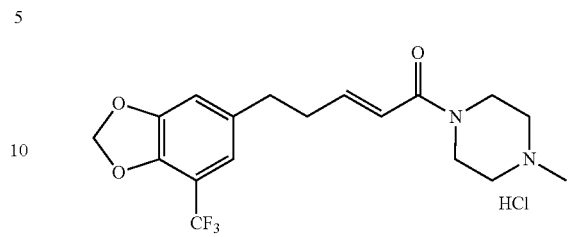

(2E, 4E)-N-isobutyl-7-(5'-trifluoromethyl-3',4'-methylenedioxy phenyl)-2,4-heptadiene amide

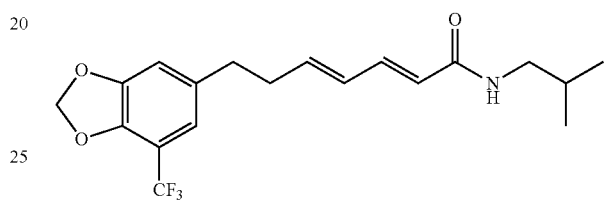

(2E,4E)-N-(4-methylpiperazinyl)-7-(5'-trifluoromethyl-3',4'-methylenedioxy phenyl)-2,4-heptadiene amide hydrochloride (II-15)

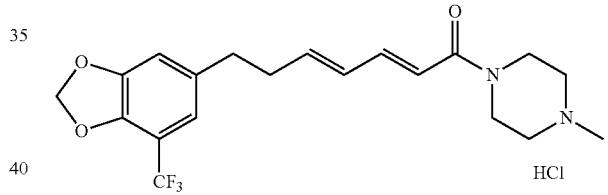

N-methyl-(5'-trifluoromethyl-3',4'-methylenedioxy)-amphetamine hydrochloride (II-16)

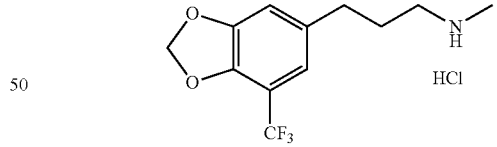

3',4'-dimethoxy-5'-trifluoromethyl-cinnamic acid isobutylamide (III-2)

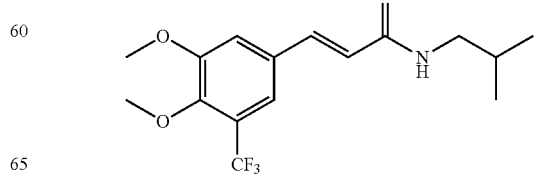

3'-hydroxyl-4'-methoxy-5'-trifluoromethyl-cinnamic acid isobutylamide (III-4)

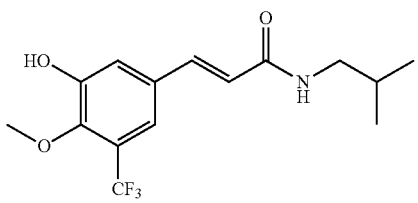 [SMILES: COc1c(O)cc(/C=C/C(=O)NCC(C)C)cc1C(F)(F)F]

3',4'-dihydroxyl-5'-trifluoromethyl-cinnamic acid isobutylamide (III-7)

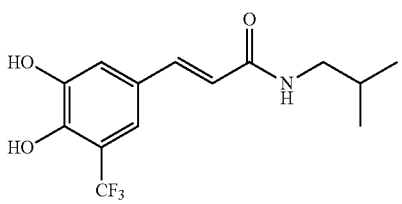 [SMILES: CC(C)CNC(=O)/C=C/c1cc(O)c(O)c(C(F)(F)F)c1]

3',4'-dihydroxyl-5'-trifluoromethyl-cinnamyl piperidine (III-9)

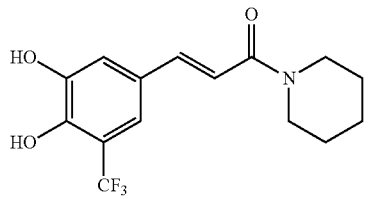 [SMILES: O=C(/C=C/c1cc(O)c(O)c(C(F)(F)F)c1)N1CCCCC1]

3-(3',4'-dihydroxyl-5'-trifluoromethyl phenyl)-propionic acid isobutylamide (III-10)

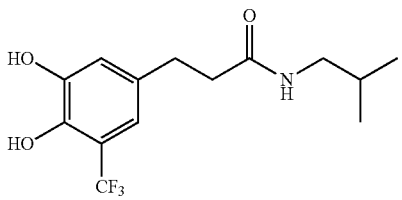 [SMILES: CC(C)CNC(=O)CCc1cc(O)c(O)c(C(F)(F)F)c1]

3,4-dihydroxyl-5-trifluoromethyl-benzoic acid isobutylamide (III-11)

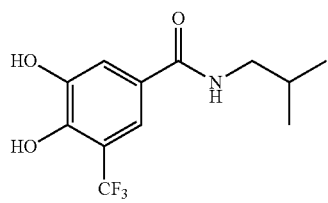 [SMILES: CC(C)CNC(=O)c1cc(O)c(O)c(C(F)(F)F)c1]

5-(5'-trifluoromethyl-3',4'-dimethoxy phenyl) pentadienoic acid isobutylamide (III-13)

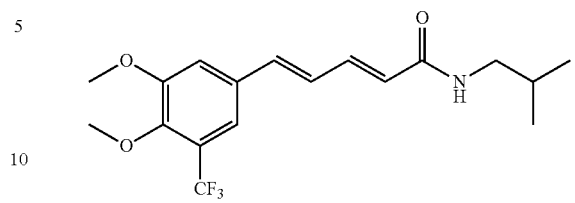

In the application of the present invention, the medications may be pharmaceutical compositions containing the compounds of the present invention or pharmaceutically acceptable salts thereof, which may be prepared into any kind of pharmaceutically acceptable dosage forms, including: tablets, capsules, granules, pills, pulvis, creams, pellets, powders, solutions, injections, suppositories, sprays, drops and patches.

As for the pharmaceutical compositions of the present invention, their preparations for oral administration may contain common excipients, such as binders, fillers, diluents, tabletting aids, lubricants, disintegrants, colorants, flavoring agents and wetting agents. Suitable fillers comprise starches, sucrose, cellulose, mannitol, lactose and other similar fillers. Suitable disintegrants comprise starches, polyvinylpyrrolidone and starch derivatives, such as sodium starch glycolate. Suitable lubricants comprise, for example, magnesium stearate. Solid oral compositions may be prepared using common methods, such as mixing, filling and tabletting etc. The mixing operation can be repeated, such that active substances are distributed throughout those compositions containing a large amount of fillers; common auxiliary ingredients comprise: mannitol, sorbitol, sodium metabisulfite, sodium bisulfite, sodium thiosulfate, cysteine hydrochloride, mercaptoacetic acid, methionine, vitamin C, EDTA disodium, EDTA calcium sodium, carbonate, acetate and phosphate of univalent alkaline metals or aqueous solutions thereof, hydrochloric acid, acetic acid, sulfuric acid, phosphoric acid, amino acids, sodium chloride, potassium chloride, sodium lactate, xylitol, maltose, glucose, fructose, dextran, glycine, starch, sucrose, lactose, mannitol, silicon derivatives, cellulose and derivatives thereof, alginate, gelatin, polyvinylpyrrolidone, glycerol, Tween 80, agar, calcium carbonate, calcium bicarbonate, surfactant, polyethylene glycol, cyclodextrin, β-cyclodextrin, phospholipids materials, kaolin, talcum powder, calcium stearate, magnesium stearate, etc.

When the preparations of the present invention are used, the usage and dosage of the preparations of the present invention are determined based on conditions, wherein these preparations may be taken 1-5 times per day.

The novel application of substituted cinnamamide derivatives provided by the present invention has the following advantages:

1. The inventor discovers that the compounds provided by the present invention can ameliorate anxiety disorders, and that these derivatives can rapidly penetrate through the blood-brain barrier, and are thus featured by rapid onset of action. Meanwhile, they also have obvious ameliorating effects on sleep disorders caused by anxiety.

2. It has been tested through assessments on animal autonomic activities that the anti-anxiety activities of the compounds provided by the present invention are not secondary results produced by their inhibiting effects on the activity of animals; in addition, when animals are fed with these compounds in a dosage of 5 g/kg, they exhibit no obvious adverse effects, indicating that these compounds have high safety and good tolerance.

3. Traditional central benzodiazepines anti-anxiety medications (e.g., diazepam) have side effects, such as sedation and muscle relaxation etc; and their clinical applications are limited.

After detecting the changes in the expressions of related genes using the Western-blot technique, it has been found that the 17 compounds described in the present invention can regulate the expressions of mitochondrial autophagy-related genes, which may be bonding ligands of peripheral benzodiazepine receptors. After bonding with the compounds described in the present invention, the peripheral benzodiazepine receptors can stimulate mitochondria to secrete steroids to regulate biological behaviors, which exhibit obvious anti-anxiety effects and have no side effects such as sedation and muscle relaxation etc.

Therefore, compared with the traditional central benzodiazepines anti-anxiety medications, the compounds described in the present invention may have advantages such as rapid onset of action, less adverse reactions and less tolerance to production and so on.

DETAILED DESCRIPTION OF THE INVENTION

The present invention is further illustrated below in combination with embodiments.

Please refer to Chinese patent CN201210123842.7 (publication number: CN102850317A) for compounds II-3, II-4, II-5, II-10, II-11 and II-12 and preparation methods thereof;

please refer to Chinese patent CN201410504555.X (publication number: CN104513172A) for compounds III-2, III-4, III-7, III-9, III-10, III-11 and III-13 and preparation methods thereof;

please refer to Embodiments 1-4 for preparation methods of compounds II-13, II-14, II-15 and II-16.

Embodiment 1: (E)-N-(4-Methylpiperazinyl)-5-(5'-Trifluoromethyl-3',4'-Methylenedioxy Phenyl)-1-Pentene Amide Hydrochloride (II-13)

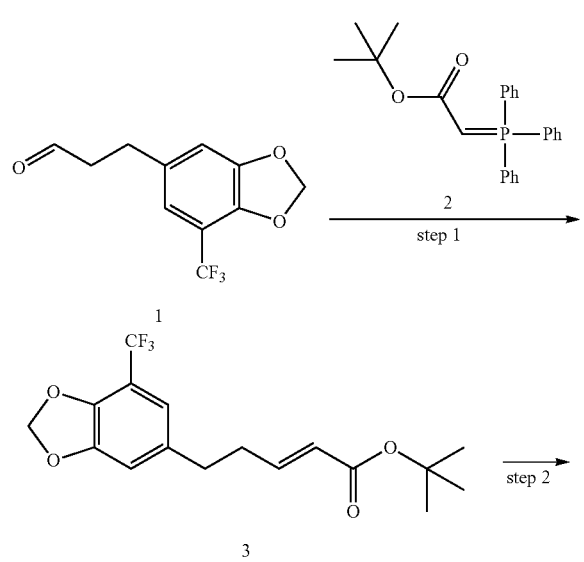

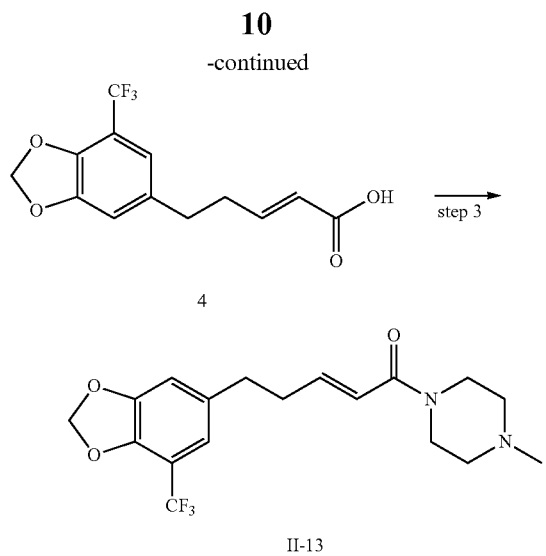

Step 1: Compound 1 (1.53 g, 4.0 mmol) was placed in a single-necked flask of 100 ml, and 15 ml of chloroform was added for dissolving; then, compound 2 (1 g, 4.0 mmol) was added into the reaction system, stirring and reacting at room temperature for 14 hours; TLC (developing solvents PE:EA=5:1) showed that the reaction was completed, then the reactants were directly concentrated to obtain a crude product compound 3; after being purified by silica gel column chromatography (PE:EA=5:1), 1.1 g of white solid compound 3 was obtained, with a yield of 78.87%.

Step 2: the compound 3 (0.3 g, 0.87 mmol) was dissolved in 5 ml of dichloromethane, and the temperature was lowered to 0°; trifluoroacetic acid (1 ml) was added dropwise into the reaction system; then, the reaction system was warmed up to room temperature for reaction; 1 hour later, after TLC showed that raw materials were completely reacted, the reaction system was directly concentrated to obtain 0.21 g of white solid compound 4 (84%).

Step 3: the compound 4 (0.48 g, 1.66 mmol), N-methylpiperazine (0.5 g, 5 mmol) and DIPEA (0.43 g, 3.34 mmol) were added into dichloromethane, and nitrogen replacement was conducted for three times; then, HATU (0.95 g, 2.5 mmol) was added and stirred at room temperature for 6 hours; the reaction system was washed with water; an organic phase was dried and concentrated to obtain a crude product; then, this crude product was purified by silica gel column chromatography to obtain 400 mg of colorless oily matter; then dissolved using 2 ml of dioxane, and 4 ml of hydrochloric acid solution of dioxane was added and stirred at room temperature for 30 minutes, concentrated and dried to obtain 43 mg of compound II-13 (65%).

$^1$H NMR (DMSO, 400 MHz): δ 11.28-11.27.00 (1H, NH, br), 7.11 (1H, s), 6.94 (1H, s), 6.70 (1H, d, J=15.2 Hz), 6.50 (1H, d, J=15.2 Hz), 6.17 (2H, s), 4.33 (2H, br), 3.42-3.20 (6H, br), 2.75 (4H, s), 2.51 (3H, s);

ESI-MS: 371.1 [M+H]$^+$

Embodiment 2: (2E,4E)-N-Isobutyl-7-(5'-Trifluoromethyl-3',4'-Methylenedioxy phenyl)-2,4-Heptadiene Amide (II-14)

Embodiment 3: (2E,4E)-N-(4-Methylpiperazinyl)-7-(5'-Trifluoromethyl-3',4'-Methylenedioxy phenyl)-2,4-heptadiene amide hydrochloride (II-15)

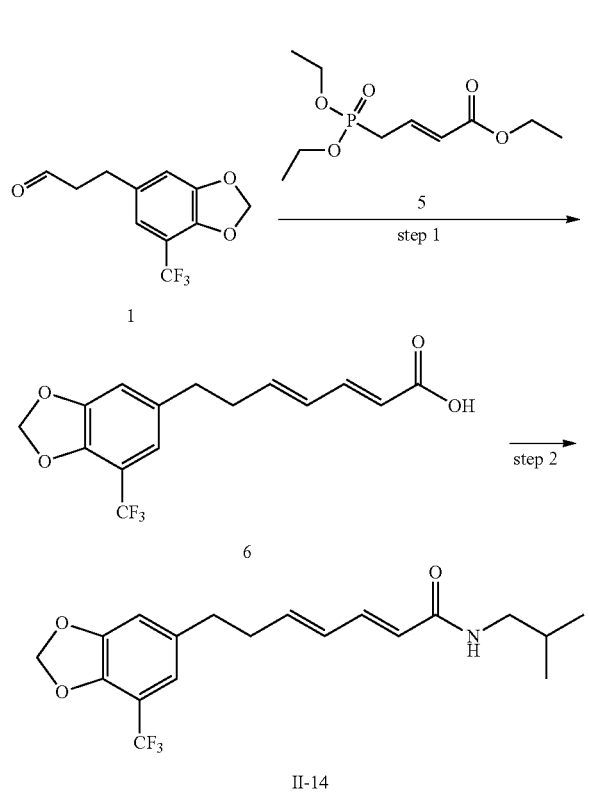

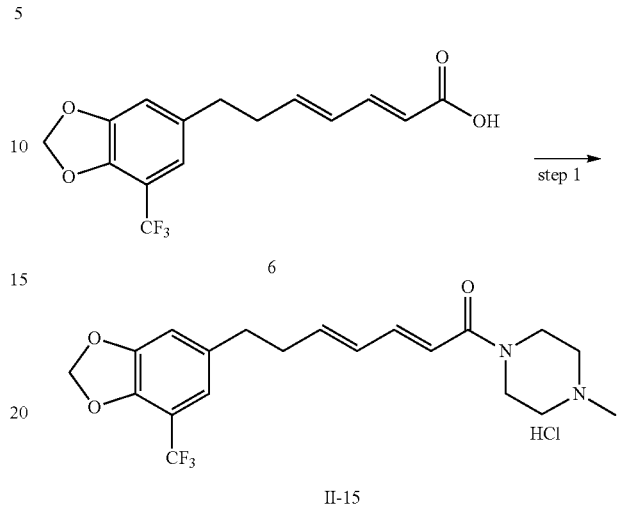

Step 1: compound 5 (650 mg, 2.6 mmol), 20 ml of anhydrous tetrahydrofuran and lithium hydroxide (326 mg, 7.8 mmol) were added into a three-necked flask of 50 ml; heated to 70° C. and reacted for 1 hours under the protection of $N_2$. The compound 1 (0.76 g, 2.0 mmol) was dissolved in 10 ml of anhydrous tetrahydrofuran, and then added dropwise into a reaction flask within half an hour. The reaction liquid was subjected to reaction at 70° C. for 10 hours. Detected by thin-layer chromatography, and heating was stopped after the reaction was completed. The reaction liquid was subjected to rotary evaporation concentration until it was dried, and then, 20 ml of distilled water was added to dissolve the solid. 2N hydrochloric acid was added dropwise slowly into the above solution until its pH value became to 2.0; continued to stir for 1 hour, and a light yellow solid was separated out; decompression and suction filtration were conducted to collect the solid, dried in vacuum to obtain a compound 6 (400 mg, 65%).

Step 2: the material 6 (400 mg, 1.4 mmol), EDCI (410 mg, 2.14 mmol) and isobutylamine (310 mg, 4.2 mmol) were dissolved into 20 ml of dichloromethane; TLC showed that the raw materials were reacted completely after being stirred and reacted at room temperature for 6 hours, the reaction system was directly concentrated to be dried; after the crude product was purified by silica gel column chromatography (n-hexane:ethyl acetate=3:1), 270 mg of white solid II-14 (52%) was obtained.

$^1$H NMR (DMSO, 400 MHz): δ 7.18 (1H, dd, $J_1$=10.8 Hz, $J_2$=4.4 Hz), 6.80 (1H, d, J=5.6 Hz), 6.11 (2H, m), 6.06 (2H, s), 5.76 (1H, d, J=15.2 Hz), 5.46 (1H, s), 3.17 (2H, t, J=6.0 Hz), 2.68 (2H, t, J=7.6 Hz), 2.44 (2H, m), 1.80 (1H, m), 0.94 (3H, s), 0.92 (3H, s);

ESI-MS: 370.1 [M+H]$^+$

The compound 6 (0.52 g, 1.66 mmol), N-methylpiperazine (0.5 g, 5 mmol) and DIPEA (0.43 g, 3.34 mmol) were added into dichloromethane; then, HATU (0.95 g, 2.5 mmol) was added and stirred at room temperature for 6 hours; the reaction system was washed with water; the organic phase was dried and concentrated to obtain a crude product; 350 mg of colorless oily matter was obtained after being purified by silica gel column chromatography; then, dissolved with 2 ml of dioxane, and 4 ml of hydrochloric acid solution of dioxane was added; stirred at room temperature for 30 minutes, and concentrated and dried to obtain 370 mg of compound II-15 (53%).

$^1$H NMR (MeOD, 400 MHz): δ 7.25 (1H, dd, $J_1$=10.8 Hz, $J_2$=4.4 Hz), 6.96 (1H, s), 6.87 (1H, s), 6.48 (1H, d, J=14.8 Hz), 6.31 (1H, dd, $J_1$=10.8 Hz, $J_2$=4.4 Hz), 6.21 (1H, m), 6.10 (2H, s), 4.87 (2H, br), 3.77-3.50 (3H, br), 3.40-3.10 (3H, br), 3.15 (3H, s), 2.76 (2H, t, J=7.2 Hz), 2.50 (2H, t, J=7.2 Hz);

ESI-MS: 397.1 [M+1]$^+$

Embodiment 4: N-Methyl-(5'-Trifluoromethyl-3',4'-Methylenedioxy)-Amphetamine Hydrochloride (II-16)

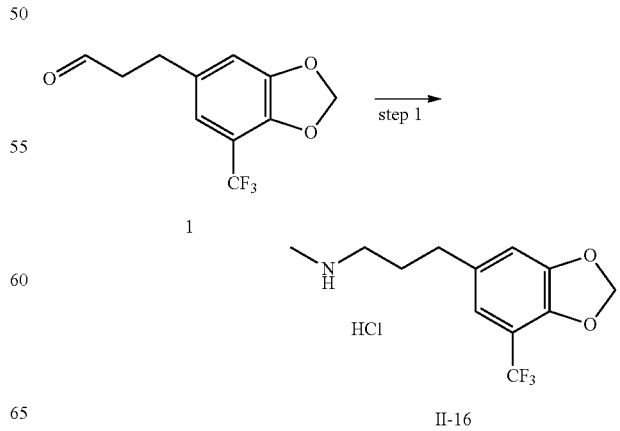

The compound 1 (650 mg, 2.6 mmol) and methylamine solution (0.4 ml, 5.1 mmol) were added into a three-necked flask of 50 ml, sodium cyanoborohydride (430 mg, 5.2 mmol) was added into 20 ml of anhydrous methanol; reacted at room temperature for 6 hours. 50 ml of water was added into the reaction liquid, organic phase was concentrated to obtain a crude product after being extracted with ethyl acetate (50 ml×2); the crude product was purified by silica gel column chromatography (n-hexane:ethyl acetate=1:1) to obtain 320 mg of oily matter; then, dissolved with 2 ml of dioxane, and 4 ml of hydrochloric acid solution of dioxane was added; stirred at room temperature for 30 minutes, concentrated and dried to obtain 340 mg of compound II-16 (47%).

$^1$H NMR (D$_2$O, 400 MHz): δ 6.93 (1H, s), 6.92 (1H, s), 6.01 (2H, s), 2.93 (2H, t, J=8.0 Hz), 2.62 (2H, t, J=8.0 Hz), 2.61 (3H, s), 1.90 (2H, m);

ESI-MS: 263.2 [M+H]$^+$

Embodiment 5: Preparation of Drop Pills 0.5 g of compound II-3, II-4, II-5, II-10, II-11, II-12, II-13, II-14, II-15, II-16, III-2, II-4, III-7, III-9, III-10, III-11 or III-13 was taken, and mixed evenly with 10.5 g of polyethylene glycol-6000, heated for fusion; the materials were moved into a drop tank for drop pills after being melted, the pharmaceutical liquid was dropped to liquid paraffin of 6-8° C., oil was removed to obtain 500 granules of drop pills.

Embodiment 6: Injections 0.5 g of compound II-3, II-4, II-5, II-10, II-11, II-12, II-13, II-14, II-15, II-16, III-2, III-4, III-7, III-9, III-10, III-11 or III-13, 4.5 g of glucose, 0.9 g of sodium thiosulfate and 1 ml of distilled water were taken; after being evenly mixed, freeze-dried and sub-packaged to obtain 500 injections.

The beneficial effects of the present invention are illustrated below by means of experimental data.

Experimental Example 1: Elevated Plus-Maze Test for Mice (I) Experimental Materials
1. Samples to be Tested Substituted cinnamamide derivatives such as compounds II-3, II-4, II-5, II-10, II-11, II-12, II-13, II-14, II-15, II-16, III-2, II-4, III-7, III-9, III-10, III-11 and III-13, were provided by the Traditional Chinese Medicine Department of the Institute of TASLY Holding Group Co., Ltd.

Sample Processing: compounds II-3, II-4, II-5, II-10, II-11, II-12, II-13, II-14, II-15, II-16, III-2, III-4, III-7, III-9, III-10, III-11 and III-13 were added into Tween 80 aqueous solution (2 wt %) to respectively formulate the above compounds into solutions with concentration of 0.5 mg/ml.

Diazepam, manufactured by: Beijing Yimin Pharmaceuticals Co., Ltd., specification: 2.5 mg/tablet, SFDA Approval Number: H11020898, formulated into a solution containing 0.075 mg/ml drug with Tween 80 aqueous solution (2 wt %) before use.

2. Experimental Animals

SPF-grade ICR male mice, purchased from Beijing Vital River Laboratory Animal Technology Co., Ltd., Production Certificate for Laboratory Animals: SCXK (JING) 2012-0001.

Raising Conditions: raised in sheltered animal houses with a temperature of 20-25° C. and a relative humidity of 40%-60%, 12 mice in each cage, free diet, feeds were sterilized complete feeds dedicated to mice, which were offered by Beijing FMK Bioscience Co., Inc.; bedding was replaced daily.

3. Experimental Instrument

Elevated plus-maze: Beijing Xintiandi Science and Technology Co., Ltd.

(II) Experimental Method

247 ICR male mice aged 6-8 weeks with the weight of 18-22 g were taken and fed adaptively for 1 week. Then, these mice were evenly divided, at random, into 19 groups based on their weights. Intragastric administration was conducted once a day according to the drugs and dosages listed in Table 1, which lasted for 7 consecutive days. 20 minutes after administration on the 7th day, the elevated plus-maze test was conducted.

The elevated plus-maze (EPM) for mice were composed of two opposite open arms (50 cm×10 cm) and two opposite enclosed arms (50 cm×10 cm×40 cm), wherein upper portions of the enclosed arms were not capped, an open portion of 10 cm×10 cm was located in the middle of the maze, and the maze was 50 cm away from the ground. The test was conducted in a quite environment at a time period ranging from 13:00 to 18:00.

Each administration group was administered continuously for 7 days, the elevated plus-maze tests were conducted with test substances 20 minutes after the final administration and positive drug diazepam 60 minutes after the final administration, each of the mice was placed in a plastic case of 60 cm×60 cm×35 cm, then placed in the center of the maze after it acquainted itself with the environment for 5 minutes. The open-arms entries (OE) and enclosed-arms entries, as well as the residence time in two arms, of the mice, within 5 minutes, were recorded respectively, and the percentage of the open-arms entries (OE %) and that of the open-arms time (OT %) for each group of mice with respect to the total entries into the two arms and the total residence time in the two arms therein were calculated respectively.

(III) Experimental Statistics

Analysis was conducted using SPSS 11.5 software, and data were represented by $\bar{x} \pm S$, the significance of differences between groups was compared using the analysis of variance, differences were significant while P was less than 0.05.

(IV) Experimental Results

In the present experiment, the effects of the 17 compounds of the present invention on the open-arms entries and the open-arms time of the mice during the elevated plus-maze test were evaluated.

TABLE 1

Effects of Various Compounds on the Open-arms Entries and the Open-arms Time of Mice

| Groups | Dosages | OE % | OT % |
|---|---|---|---|
| Solvent control groups | — | 0.53 ± 0.04 | 0.43 ± 0.06 |
| Diazepam | 1.5 mg/kg | 0.61 ± 0.06 | 0.62 ± 0.06** |
| II-3 | 10 mg/kg | 0.66 ± 0.04* | 0.66 ± 0.06** |
| II-4 | 10 mg/kg | 0.64 ± 0.04* | 0.68 ± 0.04** |
| II-5 | 10 mg/kg | 0.65 ± 0.04* | 0.69 ± 0.04** |
| II-10 | 10 mg/kg | 0.66 ± 0.04* | 0.68 ± 0.02** |
| II-11 | 10 mg/kg | 0.65 ± 0.05* | 0.65 ± 0.04** |
| II-12 | 10 mg/kg | 0.64 ± 0.02* | 0.63 ± 0.05** |
| II-13 | 10 mg/kg | 0.60 ± 0.04 | 0.58 ± 0.04* |
| II-14 | 10 mg/kg | 0.64 ± 0.03* | 0.58 ± 0.02* |
| II-15 | 10 mg/kg | 0.67 ± 0.02* | 0.68 ± 0.02** |
| II-16 | 10 mg/kg | 0.63 ± 0.02* | 0.64 ± 0.03** |
| III-2 | 10 mg/kg | 0.61 ± 0.05 | 0.58 ± 0.05* |
| III-4 | 10 mg/kg | 0.61 ± 0.03 | 0.62 ± 0.06** |
| III-7 | 10 mg/kg | 0.63 ± 0.02* | 0.60 ± 0.04* |

TABLE 1-continued

Effects of Various Compounds on the Open-arms Entries and the Open-arms Time of Mice

| Groups | Dosages | OE % | OT % |
|---|---|---|---|
| III-9 | 10 mg/kg | 0.61 ± 0.04 | 0.59 ± 0.05* |
| III-10 | 10 mg/kg | 0.64 ± 0.03* | 0.61 ± 0.04* |
| III-11 | 10 mg/kg | 0.62 ± 0.05 | 0.61 ± 0.05* |
| III-13 | 10 mg/kg | 0.66 ± 0.06* | 0.62 ± 0.05** |

Notes:
compared with the solvent control groups, *p < 0.05, and **p < 0.01.

As shown by the experimental results of Table 1, compared with the solvent control groups, after intragastric administration with the compounds II-3, II-4, II-5, II-10, II-11, II-12, II-13, II-14, II-15, II-16, III-2, III-4, III-7, III-9, III-10, III-11 and III-13 of the present invention for 1 week in a dosage of 10 mg/kg, they all could increase the open-arms entries of the mice, and prolong their open-arms time, the above results had significant differences in statistics (p<0.05, and p<0.01).

Experimental Conclusion: In the elevated plus-maze test, after the 17 compounds described in the present invention were administered for 7 days in a dosage of 10 mg/kg, they could, in varying degrees, increase the open-arms entries of the mice and prolong their open-arms time during the elevated plus-maze test.

It could be proved by the experimental results that, the 17 compounds described in the present invention had significant anti-anxiety activities.

Experimental Example 2: Drinking Conflict Experiment for Rats (I) Experimental Materials
1. Samples to be Tested Substituted cinnamamide derivatives such as compounds II-3, II-4, II-5, II-10, II-11, II-12, II-13, II-14, II-15, II-16, III-2, III-4, III-7, III-9, III-10, III-11 and III-13, were provided by the Traditional Chinese Medicine Department of the Institute of TASLY Holding Group Co., Ltd.

Sample Processing: compounds II-3, II-4, II-5, II-10, II-11, II-12, II-13, II-14, II-15, II-16, III-2, III-4, III-7, III-9, III-10, III-11 and III-13 were added into Tween 80 aqueous solution (2 wt %) to respectively formulate the above compounds into solutions with concentration of 0.5 mg/ml.

Diazepam, manufactured by: Beijing Yimin Pharmaceuticals Co., Ltd., specification: 2.5 mg/tablet, SFDA Approval Number: H11020898, formulated into a solution containing 0.01 mg/ml drug with Tween 80 aqueous solution (2 wt %) before use.

2. Experimental Animals

SPF-grade male SD rats, purchased from Beijing Vital River Laboratory Animal Technology Co., Ltd., Production Certificate for Laboratory Animals: SCXK (JING) 2012-0001.

Raising Conditions: raised in sheltered animal houses with a temperature of 20-25° C. and a relative humidity of 40%-60%, 6 rats in each cage, free diet, feeds were sterilized complete feeds dedicated to rats, which were offered by Beijing HFK Bioscience Co., Inc.; bedding was replaced daily.

3. Experimental Instrument

Vogel test anxiety testing system, model: LE100-25, produced by Harvard Apparatus of the U.S.A.

(II) Experimental Method

230 SD male rats with the weight of 180-220 g were taken and fed adaptively for 1 week. Then, these rats were divided, at random, into 19 groups based on their weights, 12-13 rats in each group. Intragastric administration was conducted one a day according to the drugs and dosages listed in Table 2, which lasted for 10 consecutive days. Water deprivation 48 hours before the final administration, and non-punitive drinking training was conducted on the 9th day; on the 10th day, half an hour after the final intragastric administration of all the groups, the punitive experimental test was conducted.

On the first stage (non-punitive drinking training): after water deprivation for 24 hours, the rats were placed in operation boxes individually to explore thoroughly, until they found bottle mouths and began to lick water, water licks of the rats within 3 minutes under the conditions of no electric shock (the condition was set as follows: the strength of electric shock was 0 mA) were automatically recorded by counters, and rats whose water licks were less than 300 were eliminated. On the second stage (punitive experiment): the above rats which were not eliminated were placed in the operation boxes after continuing the water deprivation for 24 hours (48 hours in total). The rats could find the bottle mouths rapidly and begin to lick water, the instruments began to time automatically and imparted one electric shock (the ratio of licks to the number of electric shocks was 20:1) while the water licks reached to 20, wherein the strength of electric shocks was 0.3 mA, lasting for 2 seconds, but these rats may control the length of the time for which they were electrically shocked by keeping away from the bottle mouths. Water licks of the rats during the punished session (3 minutes) were recorded.

Observational indexes of the Vogel drinking conflict model: water licks of the rats during the punished session.

(III) Experimental Statistics

Analysis was conducted using SPSS 11.5 software, and data were represented by $\bar{x} \pm S$, the significance of differences between groups was compared using the analysis of variance, differences were significant while P was less than 0.05.

(IV) Experimental Results

In the present experiment, the effects of the 17 compounds of the present invention on the water licks of the rats during the punished session of the drinking conflict experiment were evaluated.

TABLE 2

Effects of Various Compounds on Water Licks of Rats During Punished Session

| Groups | Dosages | Number of rats | Water licks |
|---|---|---|---|
| Solvent control groups | — | 8 | 310.75 ± 45.14 |
| Diazepam | 1 mg/kg | 9 | 510.22 ± 48.43** |
| II-3 | 5 mg/kg | 8 | 483.75 ± 59.05** |
| II-4 | 5 mg/kg | 10 | 477.22 ± 66.66** |
| II-5 | 5 mg/kg | 9 | 469.11 ± 50.51** |
| II-10 | 5 mg/kg | 8 | 459.75 ± 59.23** |
| II-11 | 5 mg/kg | 8 | 426.25 ± 37.29** |
| II-12 | 5 mg/kg | 10 | 402.67 ± 50.35** |
| II-13 | 5 mg/kg | 9 | 393.44 ± 48.99** |
| II-14 | 5 mg/kg | 9 | 368.00 ± 47.38* |
| II-15 | 5 mg/kg | 8 | 412.25 ± 42.90** |
| II-16 | 5 mg/kg | 9 | 406.56 ± 65.38** |
| III-2 | 5 mg/kg | 9 | 368.00 ± 39.59* |
| III-4 | 5 mg/kg | 10 | 394.22 ± 50.29** |
| III-7 | 5 mg/kg | 10 | 378.33 ± 54.97* |
| III-9 | 5 mg/kg | 9 | 363.56 ± 39.70* |
| III-10 | 5 mg/kg | 8 | 369.00 ± 44.83* |

TABLE 2-continued

Effects of Various Compounds on Water Licks of Rats During Punished Session

| Groups | Dosages | Number of rats | Water licks |
|---|---|---|---|
| III-11 | 5 mg/kg | 8 | 361.13 ± 38.38* |
| III-13 | 5 mg/kg | 9 | 375.67 ± 58.13* |

Notes:
When compared with the solvent control groups, *p < 0.05, and **p < 0.01.

As shown by the experimental results of Table 2, compared with the solvent control groups, after intragastric administration with the compounds II-3, II-4, II-5, II-10, II-11, II-12, II-13, II-14, II-15, II-16, III-2, III-4, III-7, III-9, III-10, III-11 and III-13 of the present invention for 10 days in a dosage of 5 mg/kg, they all could increase water licks of the rats during the punished session, and the above results had significant differences in statistics (p<0.05, and p<0.01).

Experimental Conclusion: In the drinking conflict experiment for rats, after the 17 compounds described in the present invention were administered for 10 days in a dosage of 5 mg/kg, they all could, in varying degrees, increase water licks of the rats during the punished session.

It could be proved by the experimental results that, the 17 compounds described in the present invention had anti-anxiety activities.

The invention claimed is:

1. A method of ameliorating a disorder, comprising administering a pharmaceutical composition comprising a substituted cinnamamide derivative to a subject in need thereof, wherein the disorder is an anxiety disorder, and, wherein the substituted cinnamamide is a compound selected from the group consisting of 5'-iodine-3',4'-methylenedioxy cinnamic acid isobutylamide (II-3),

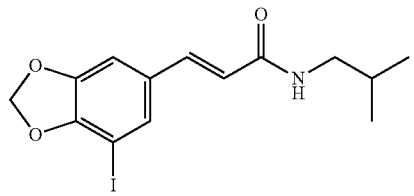 [SMILES: CC(C)CNC(=O)/C=C/c1cc(I)c2c(c1)OCO2]

5'-chlorine-3',4'-methylenedioxy cinnamic acid isobutylamide (II-4),

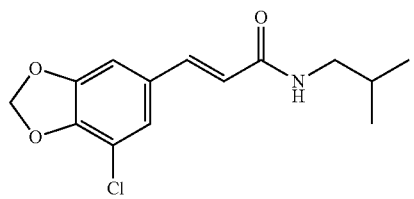 [SMILES: CC(C)CNC(=O)/C=C/c1cc(Cl)c2c(c1)OCO2]

5'-trifluoromethyl-3',4'-methylenedioxy cinnamic acid isobutylamide (II-5),

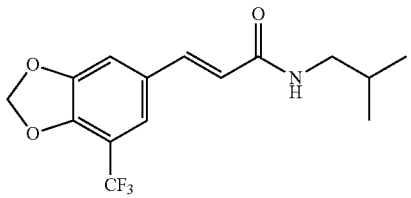

5'-trifluoromethyl-3',4'-methylenedioxy cinnamic acid piperidylamide (II-10),

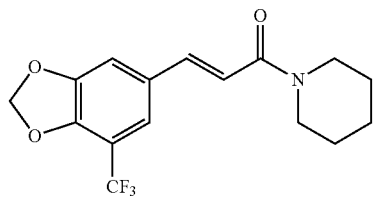

3-(5'-trifluoromethyl-3',4'-methylenedioxy phenyl)-propionic acid isobutylamide (II-11), and

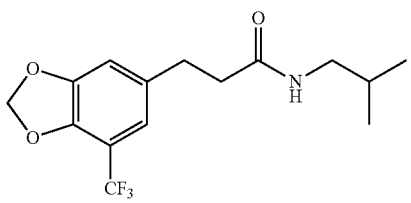

5-trifluoromethyl-3',4'-methylenedioxy benzoic acid isobutylamide (II-12)

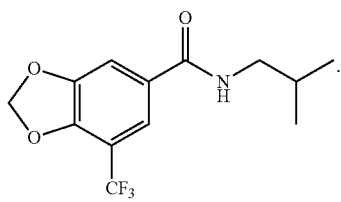 [SMILES: CC(C)CNC(=O)c1cc2c(c(C(F)(F)F)c1)OCO2]

2. The method of claim 1, wherein the anxiety disorder is chronic anxiety or acute anxiety.

3. The method of claim 1, wherein the pharmaceutical formulation consists of a dosage form selected from the group consisting of a tablet, capsule, granule, pill, pulvis, cream, pellet, powder, solution, injection, suppository, spray, drop, and patch.

4. The method of claim 1, wherein the pharmaceutical formulation further comprises polyethylene glycol and paraffin and consists of a pill.

5. The method of claim 1, wherein the pharmaceutical formulation further comprises sodium thiosulfate and distilled water and consists of a solution for injection.

6. The method of claim 1, wherein the pharmaceutical formulation is administered 1-5 times per day.

7. The method of claim 1, wherein the anxiety disorder displays as emotional symptoms selected from the group consisting of jitters, scariness, terror, fear and apprehensiveness.

8. The method of claim 1, wherein the anxiety disorder displays as vegetative nervous symptoms selected from the group consisting of dizziness, chest distress, palpitation, tachypnea, dry mouth, frequent urination, urgent urination, sweating and tremor.

9. The method of claim 1, wherein the anxiety disorder displays as psychomotor anxiety selected from the group consisting of restlessness, uneasiness, irritability, and difficulties in staying calm.

\* \* \* \* \*